(12) United States Patent
Guo et al.

(10) Patent No.: US 12,285,349 B2
(45) Date of Patent: Apr. 29, 2025

(54) LUMBAR SUPPORT BELT

(71) Applicant: Yacca Medical (Shenzhen) Co., Ltd., Shenzhen (CN)

(72) Inventors: Yue Guo, Shenzhen (CN); Jianlong Yao, Shenzhen (CN); Ling Bai, Shenzhen (CN)

(73) Assignee: YACCA MEDICAL (SHENZHEN) CO., LTD., Shenzhen (CN)

( * ) Notice: Subject to any disclaimer, the term of this patent is extended or adjusted under 35 U.S.C. 154(b) by 399 days.

(21) Appl. No.: 17/826,149

(22) Filed: May 26, 2022

(65) Prior Publication Data

US 2022/0280327 A1 Sep. 8, 2022

Related U.S. Application Data

(63) Continuation-in-part of application No. PCT/CN2020/129655, filed on Nov. 18, 2020.

(30) Foreign Application Priority Data

Nov. 29, 2019 (CN) .......................... 201911197632.0

(51) Int. Cl.
*A61F 5/02* (2006.01)

(52) U.S. Cl.
CPC .................... *A61F 5/028* (2013.01)

(58) Field of Classification Search
CPC .. A61F 5/01; A61F 5/012; A61F 5/028; A61F 5/03; A61F 5/02; A61F 5/022; A61F 2250/001; A41C 1/00; A41C 1/08; A41C 1/12; A41D 2400/38
USPC ............ 602/5, 6, 13, 19; 450/154; 128/96.1, 128/845, 870, 876
See application file for complete search history.

(56) References Cited

U.S. PATENT DOCUMENTS

| | | | |
|---|---|---|---|
| 2002/0087105 A1* | 7/2002 | Grosso | A61F 5/34 602/5 |
| 2010/0217167 A1* | 8/2010 | Ingimundarson | A61F 5/028 602/19 |
| 2012/0253251 A1* | 10/2012 | Thornton | A61F 5/028 602/19 |

FOREIGN PATENT DOCUMENTS

WO    WO-0062642 A1 * 10/2000    ............... A45F 3/02

* cited by examiner

*Primary Examiner* — Caitlin A Carreiro
(74) *Attorney, Agent, or Firm* — MATTHIAS SCHOLL P.C.; Matthias Scholl

(57) ABSTRACT

A lumbar support belt includes a back belt, a first waist belt, a second waist belt, and a tightening mechanism. The first waist belt and the second waist belt are connected to two ends of the back belt, respectively, to wrap around the waist and the abdomen of a user. The back belt is a plastic support board. The first waist belt includes a first front part and the second waist belt includes a second front part. The first front part and the second front part are attached to each other to form a compression belt abutting against the abdomen of the user. The first waist belt includes a first back part and the second waist belt includes a second back part. The first back part and the second back part are disposed at a distance from the support board.

10 Claims, 15 Drawing Sheets

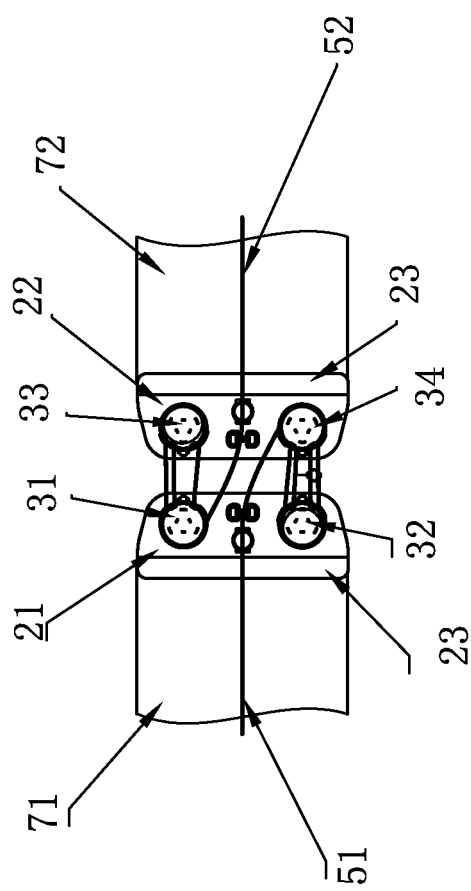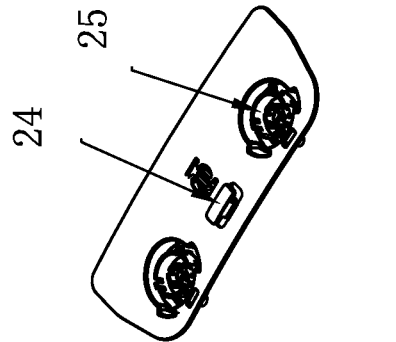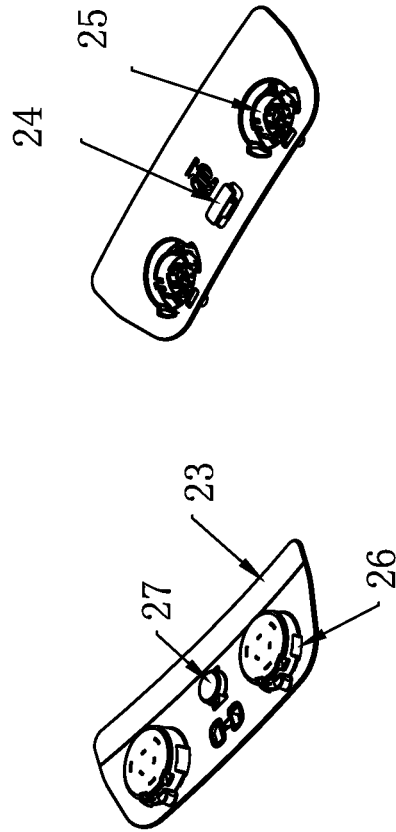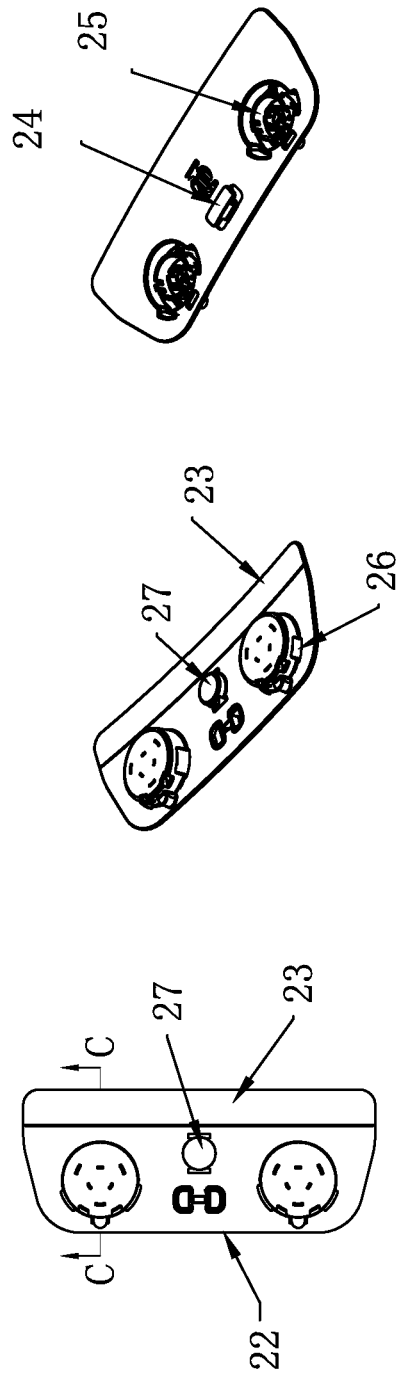
FIG. 7A
FIG. 7B
FIG. 7C
FIG. 7D

LUMBAR SUPPORT BELT

CROSS-REFERENCE TO RELATED APPLICATIONS

This application is a continuation-in-part of International Patent Application No. PCT/CN2020/129655 with an international filing date of Nov. 18, 2020, designating the United States, now pending, and further claims foreign priority benefits to Chinese Patent Application No. 201911197632.0 filed Nov. 29, 2019. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, MA 02142.

BACKGROUND

The disclosure relates to a back protector; and more particularly, to a lumbar support belt comprising a tightening mechanism.

People with injuries to the lumbar vertebrae need a long time to recover after surgery. To prevent secondary injury, e.g., lumbar sprain or impact injuries, patients choose to wear lumbar support belts to support their waists. Conventional lumbar support belts include:

1. Rigid Brace

A conventional rigid brace is heavy and uncomfortable, causing abdominal atrophy after a long time use, so that the conventional rigid brace is only suitable for use in an acute phase after surgery.

2. Stretchable Belt

A conventional stretchable belt is a one-piece structure made of knitted fabrics and comfortable to wear. The stretchable belt includes a multi-layered back support section; a plurality of vertical steel strips is fixed at intervals in the multi-layer structure to support the waist; the plurality of steels strips is arc-shaped and sewn into the back support section. The conventional stretchable belt further includes a left waist belt and a right waist belt which are provided with a hook and a loop of a hook-loop fastener, respectively; in use, the back support section is fixed on the lower back; and the left waist belt is attached to the right waist belt through the hook-loop fastener.

In addition, the back support section includes the steel strips which are not air permeable, so that the lumbar support belt must be removed from a patient in case of a magnetic resonance imaging (MRI), which may lead to secondary injury.

SUMMARY

The disclosure provides a lumbar support belt fitting different body shapes, and the lumbar support belt comprises a tightening mechanism which can provide support and pressure to the abdomen and waist of a user.

The lumbar support belt comprises a back belt, a first waist belt, a second waist belt, and a tightening mechanism; the first waist belt and the second waist belt are connected to two ends of the back belt, respectively, to wrap around a waist and an abdomen of a user. The first waist belt and the second waist belt are adjustable in length; the back belt is a plastic support board; the first waist belt comprises a first front part and the second waist belt comprises a second front part; the first front part and the second front part are attached to each other to form a compression belt abutting against the abdomen of the user; the first waist belt comprises a first back part and the second waist belt comprises a second back part; the first back part and the second back part are disposed at a distance from the support board; the first back part and the second back part are connected to the support board through the tightening mechanism; and when in use, the lumbar support belt is wrapped around the waist, the tightening mechanism is tightened or loosened to control the support board and the compression belt to press the waist and abdomen.

In a class embodiment of this disclosure, the first front part or the second front part comprises an abdominal compression board being plastic, and the abdominal compression board is attached to the compression belt.

In a class embodiment of this disclosure, each of the first waist belt and the second waist belt comprises a first part and a second part sewn onto the first part; the first part comprises a first stretch fabric; the second part comprises a second stretch fabric; the elastic deformation of the first stretch fabric is larger than that of the second stretch fabric; and the compression belt employs the second stretch fabric.

In a class embodiment of this disclosure, the tightening mechanism is plastic, and comprises a first connecting plate and a second connecting plate which are of the same shape and have the same curvature as the support board.

In a class embodiment of this disclosure, the first connecting plate comprises a first fixed end and a first free end; the first fixed end is connected to one end of the first waist belt; the first connecting plate comprises an inner surface comprising a first sliding block; the support board comprises a first horizontal groove; the first sliding block is disposed into the first horizontal groove and is configured to slide back and forth to drive the first connecting plate to move horizontally on the waist; and the first connecting plate further comprises at least one first group of pulleys.

In a class embodiment of this disclosure, the second connecting plate comprises a second fixed end and a second free end; the second fixed end is connected to one end of the second waist belt; the second connecting plate comprises an inner surface comprising a second sliding block; the support board comprises a second horizontal groove; the second sliding block is disposed into the second horizontal groove and is configured to slide back and forth to drive the second connecting plate to move horizontally on the waist; and the second connecting plate further comprises at least one second group of pulleys.

In a class embodiment of this disclosure, the lumbar support belt further comprises a drawstring wrapped around the first group of pulleys and the second group of pulleys; when the drawstring is pulled tighten, the first connecting plate and the second connecting plate move towards each other.

In a class embodiment of this disclosure, the first group of pulleys comprises a first upper group of pulleys and a first lower group of pulleys which are disposed on the upper and lower parts of the first connecting plate, respectively; the second group of pulleys comprises a second upper group of pulleys and a second lower group of pulleys which are disposed on the upper and lower parts of the second connecting plate, respectively; the drawstring comprises a first drawstring and a second drawstring; the first drawstring is wrapped around the first upper group of pulleys and the second upper group of pulleys to pull tighten or loosen the upper part of the first connecting plate and the upper part of the second connecting plate; and the second drawstring is wrapped around the first lower group of pulleys and the second lower group of pulleys to pull tighten or loosen the lower parts of the first connecting plate and the second connecting plate.

In a class embodiment of this disclosure, the first group of pulleys and the second group of pulleys each comprise a first pulley and a second pulley having a smaller diameter than the first pulley; the first pulley and the second pulley are coaxial; an axial line of the first pulley and the second pulley is perpendicular to the direction of motion of the first connecting plate or the second connecting plate; each connecting plate comprises an outer surface and an inner surface; the outer surface protrudes to form a cavity and the cavity extends through the inner surface; a sidewall connecting the inner surface and the outer surface comprises a plurality of notches; the drawstring comprises a first end and a second end; and the second end of the drawstring passes through at least one of the plurality of notches so that the drawstring is wrapped around the first group of pulleys and the second group of pulleys.

In a class embodiment of this disclosure, the lumbar support belt further comprises a height-adjustable board disposed on the support board; the support board further comprises a plurality of locating holes spaced apart from each other; the height-adjustable board comprises at least one locating block; the at least one locating block is inserted into the plurality of locating holes to adjust the height of the height-adjustable board relative to the support board.

In a class embodiment of this disclosure, the lumbar support belt further comprises a box for receiving the drawstring; the first end of the drawstring is secured to the box; the box comprises a bottom surface provided with a hook of a hook-loop fastener; each of the first waist belt and the second waist belt comprises an outer surface provided with a loop of the hook-loop fastener; and the hook of the box is attached to the loop of each waist belt.

In a class embodiment of this disclosure, the lumbar support belt further comprises a wire hinge disposed on each end of the compression belt to control the tightening mechanism.

In a class embodiment of this disclosure, the support board, the abdominal compression board, and the height-adjustable board each comprise a plurality of vent holes.

In a class embodiment of this disclosure, the support board further comprises an inner surface comprising an airbag cushion.

In a class embodiment of this disclosure, the lumbar support belt further comprises a belt cutting template used in combination with a pair of scissors to cut an overlong part of the first waist belt and the second waist belt.

The support board comprises a rigid material for supporting the waist; the first waist belt is connected to the second waist belt through the tightening mechanism; the front parts of the first waist belt and the second waist belt are attached together through a hook-loop fastener. In use, the lumbar support belt is wrapped around the waist; when the drawstring is pulled tighten, the abdominal compression board and the support board apply uniform forces on the abdomen and the waist to protect the lumbar vertebrae, respectively; the height-adjustable board is raised or lowered relative to the support board to fit different waist heights; the first drawstring and the second drawstring are pulled tighten or loosened to change the shape of a gap formed between the first connecting plate and the second connecting plate, so that the lumbar support belt fits different body shapes.

DETAILED DESCRIPTION OF THE DRAWINGS

FIG. 7A is a front view of a tightening structure in an unloaded instate;

FIG. 7B is a front view of a second connecting plate in FIG. 7A;

FIG. 7C is a perspective view of a second connecting plate in FIG. 7A;

FIG. 7D is a bottom view of a second connecting plate in FIG. 7C;

Figure 1:
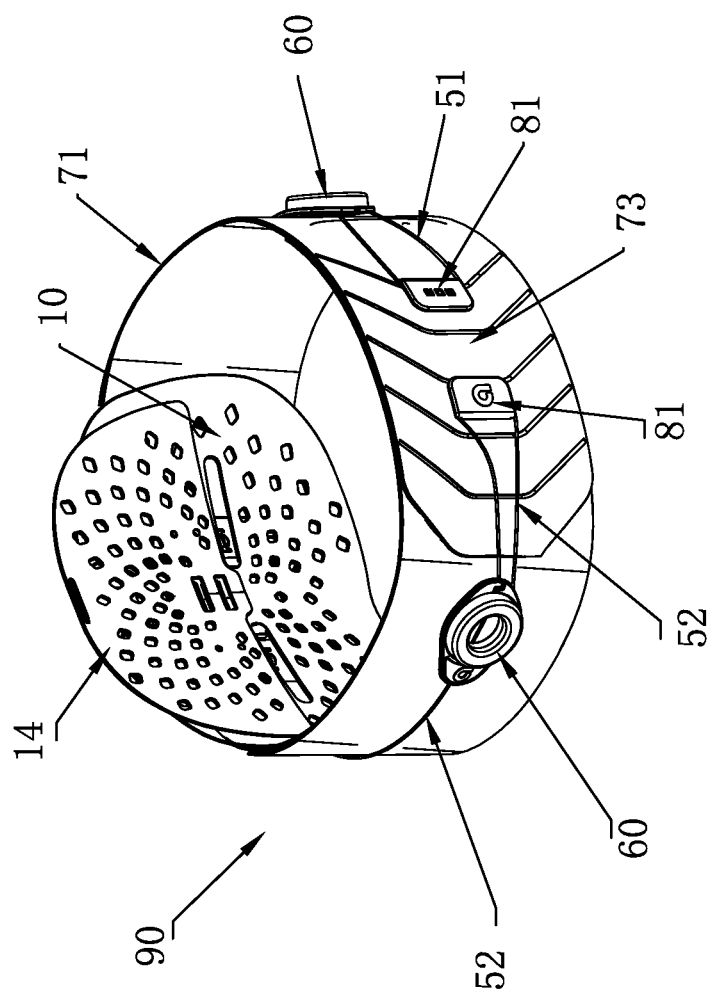
FIG. 1 is a perspective view of a lumbar support belt of the disclosure.

In the drawings, the following reference numbers are used: 1. Support board; 11. Locating hole; 12. Groove; 13. Height-adjustable board; 14. Vent hole; 15. Airbag cushion; 21. First connecting plate; 22. Second connecting plate; 23. Clipping plate; 24. Sliding block; 25. Cavity; 26. Notch; 27. Guide hole or guide groove; 31. First upper group of pulleys; 32. First lower group of pulleys; 33. Second upper group of pulleys; 34. Second lower group of pulleys; 41. First pulley; 42. Second pulley; 51. First drawstring; 52. Second drawstring; 60. Box; 61. Base; 62. Fixing ring; 63. Rubber sleeve; 64. First hole; 65. Clamping block; 66. Buckle; 67. String hole; 71. First waist belt; 72. Second waist belt; 73. Compression belt; 74. First stretch fabric; 75. Second stretch fabric; 76. Belt cutting template; 761. Hole; 762. Cutting side; 763. Reference side; 80. Abdominal compression board; 81. Wire hinge; and 90. Lumbar support belt.

DETAILED DESCRIPTION

To further illustrate, embodiments detailing a lumbar support belt are described below. It should be noted that the following embodiments are intended to describe and not to limit the disclosure.

Figure 2:
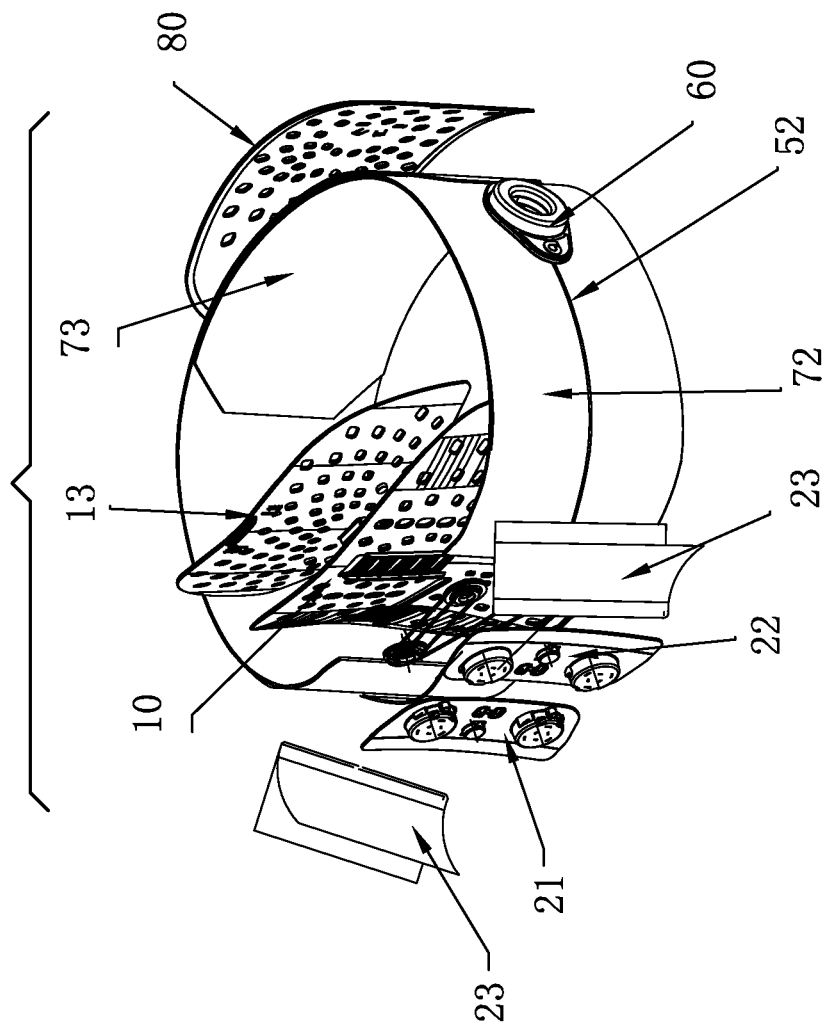
FIG. 2 is an exploded view of a lumbar support belt in FIG. 1.
Figure 3:
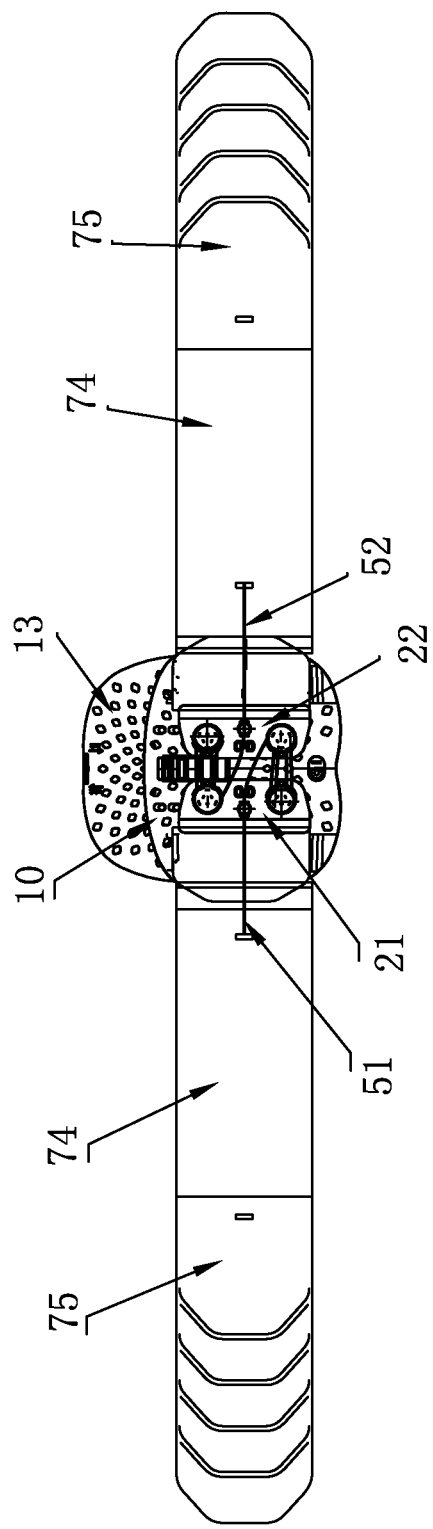
FIG. 3 is an unfolded view of a lumbar support belt in FIG. 1.

As shown in FIGS. 1-3, a lumbar support belt 90 comprises a back belt, a tightening mechanism, a drawstring, a first waist belt 71, a second waist belt 72, and an abdominal compression board 80.

1. Back Belt

1) Material and Thickness

The back belt is a support board 10 comprising a rigid plastic material with elasticity; the support board 10 is in the shape of an arc designed to achieve an ergonomic setup; the support board 10 comprises a plurality of vent holes 14 in the shape of rhombus; and the support board 10 comprises a middle part and two both ends thinner than the middle part.

The middle part has a thickness of less than 2.5 mm, and the both ends each have a thickness of less than 2.0 mm.

2) Arc-Shaped Inner Surface

Figure 4:
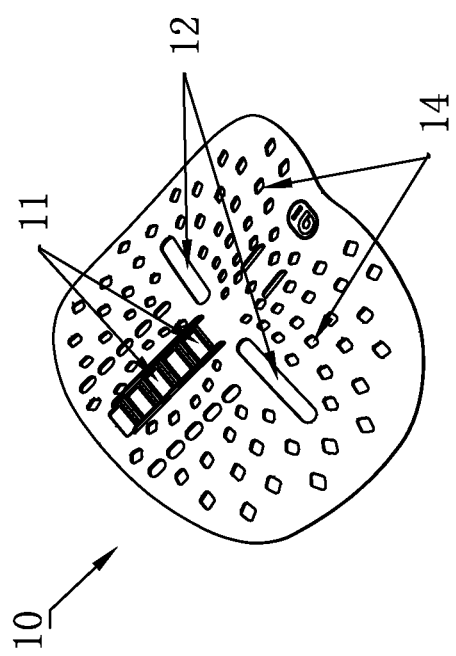
FIG. 4 is a perspective view of a support board in FIG. 1.
Figure 5:
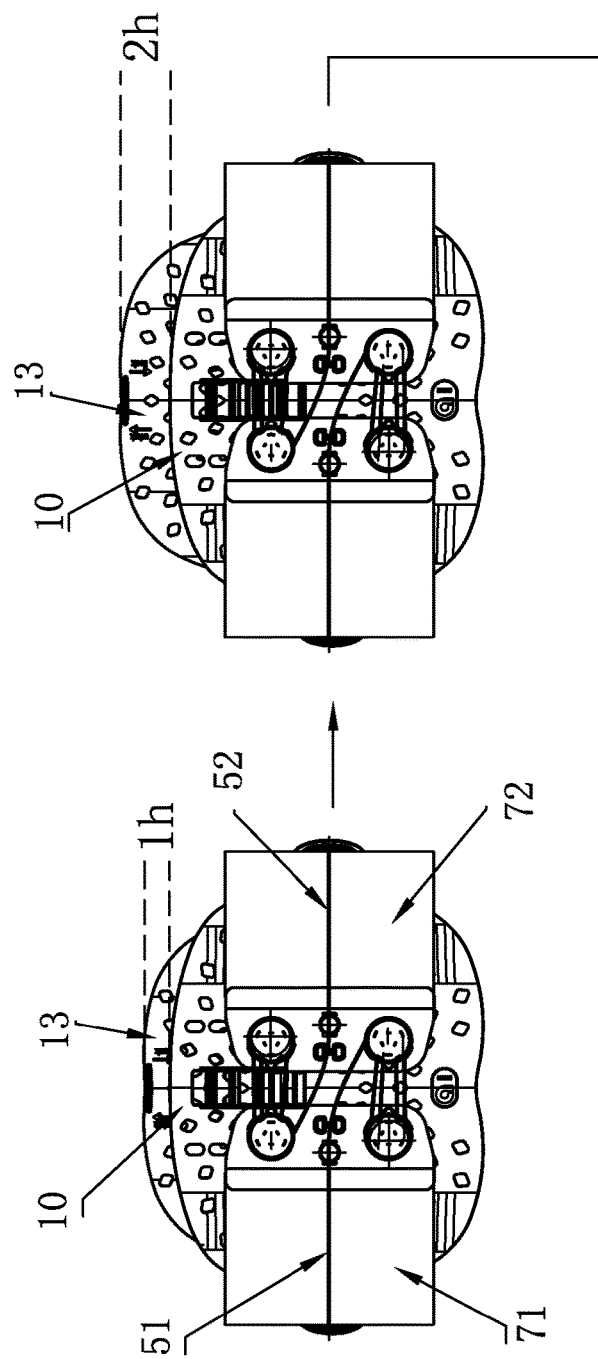
FIG. 5 is a front view of a support boards that is raised by four different heights.
Figure 5:
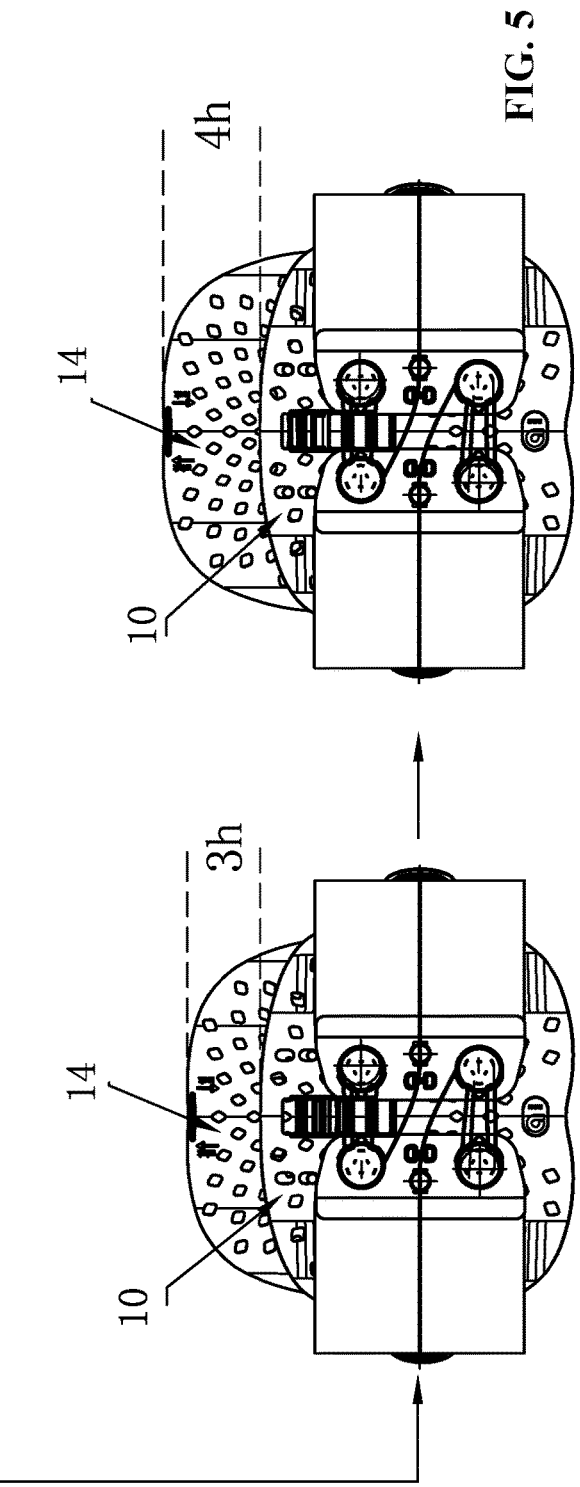

As shown in FIGS. 2, 4, and 5, the support board 10 comprises an inner hyperboloid that is divided into left and right parts by a central axis parallel to the lumbar vertebrae; the left and right parts extend toward both sides of the waist, respectively; the support board 10 is divided into upper and lower parts that are bent backward from a horizontal plane where the third or fourth lumbar vertebra is located; and the thickness of the support board 10 has a maximum magnitude in the middle part and gradually decreases towards the both ends, so that the support board 10 fits different body shapes to support their waists.

3) Height-Adjustable Board 13

The support board 10 further comprises a height-adjustable board that is raised or lowered relative to the support board 10 (as shown in FIG. 5).

The height-adjustable board and the support board 10 are of the same thickness and of the same material; the height-adjustable board comprises a plurality of vent holes 14 and an inner surface in the same shape as the upper part of the inner hyperboloid of the support board 10.

The support board 10 further comprises a plurality of locating holes 11 disposed at intervals on the central axis; the height-adjustable board comprises at least two locating blocks detachably disposed in the plurality of locating holes 11 to fix the height-adjustable board 13 on the inner hyperboloid of the support board 10. The at least two locating blocks are inserted into the different locating holes 11 to raise or lower the height-adjustable board 13 relative to the support board 10.

The height-adjustable board 13 may be raised by four heights, including 1 h-4 h (as shown in FIG. 5).

4) Groove 12

The support board 10 further comprises a groove 12 disposed below and perpendicular to the straight line where the plurality of locating holes 11 is located. In an alternative preferred embodiment of the disclosure, the groove 12 is divided into a left groove 12 and a right groove 12 which are spaced apart from each other.

5) Airbag Cushion 15

Figure 13:
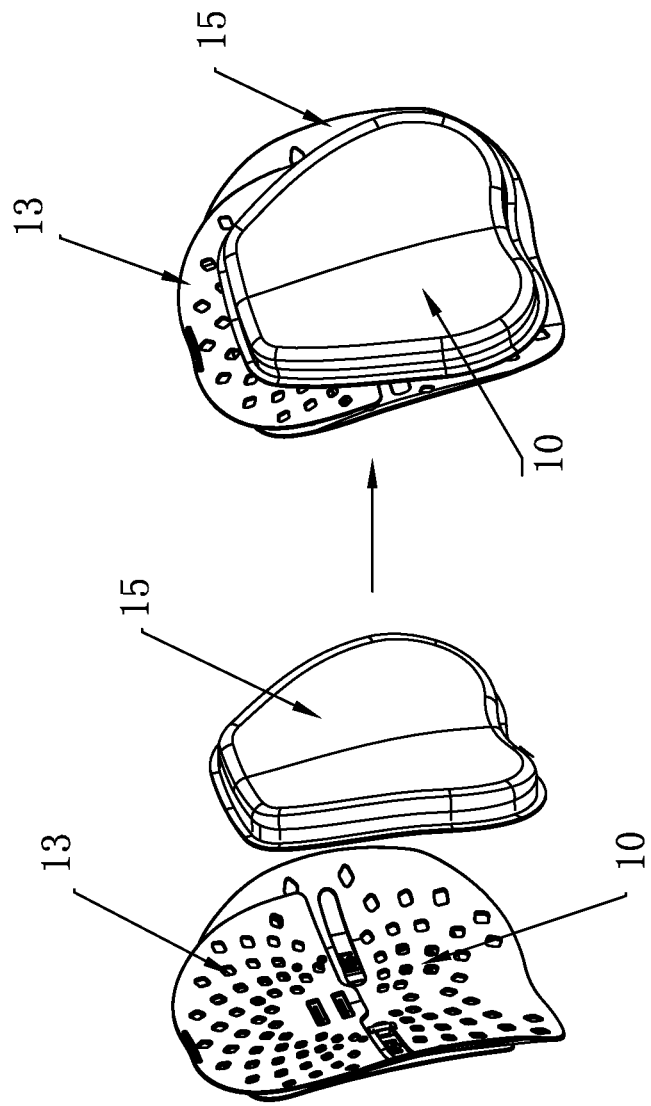
FIG. 13 is a perspective view of an airbag cushion according to one example of the disclosure.

As shown in FIG. 13, the support board 10 further comprises an airbag cushion 15 and an outer side; the airbag cushion 15 is disposed on the outer side to contact with the back waist; the airbag cushion 15 has a thickness of 25-25 mm in the inflated state, which makes the support board 10 fit different body shapes, thus enhancing user's experience.

2. Tightening Mechanism

As shown in FIGS. 6, 7A, 7B, 7C, 7D, 8 and 9, the tightening mechanism comprises a first connecting plate 21, a second connecting plate 22, and the drawstring; the first connecting plate 21 and the second connecting plate 22 are disposed on both sides of the support board 10 and each comprise a group of pulleys; the drawstring is wrapped around the two groups pf pulleys, and pulled tighten or loosened, so that the first connecting plate 21 and the second connecting plate 22 are moved closer or farther away from each other.

1) Connecting Plate

The first connecting plate 21 and the second connecting plate 22 comprise plastic materials, have rectangular cross sections, and have the same inner hyperboloid as the left and right parts of support board 10, respectively, so that the first connecting plate 21 and the second connecting plate 22 fit the shape of the support board 10 and move smoothly.

The tightening mechanism further comprises a clipping plate 23 whose one end is fixedly attached to the first connecting plate 21 by gluing, hot pressing, sewing, or screwing; the clipping plate 23 is a double-plywood structure in which the inner side comprises a loop of a hook-loop fastener; the first waist belt 71 further comprises a first end provided with a hook of a hook-loop fastener; the hook of the first waist belt is attached to the loop of the clipping plate 23 to ensure the first waist belt 71 is fixedly connected to the first connecting plate 21 (as shown in FIG. 2). The tightening mechanism further comprises another clipping plate 23 fixedly attached to on one end of the second connecting plate 22 and to a first end of the second waist belt 72 through the hook-loop fastener.

Figure 10:
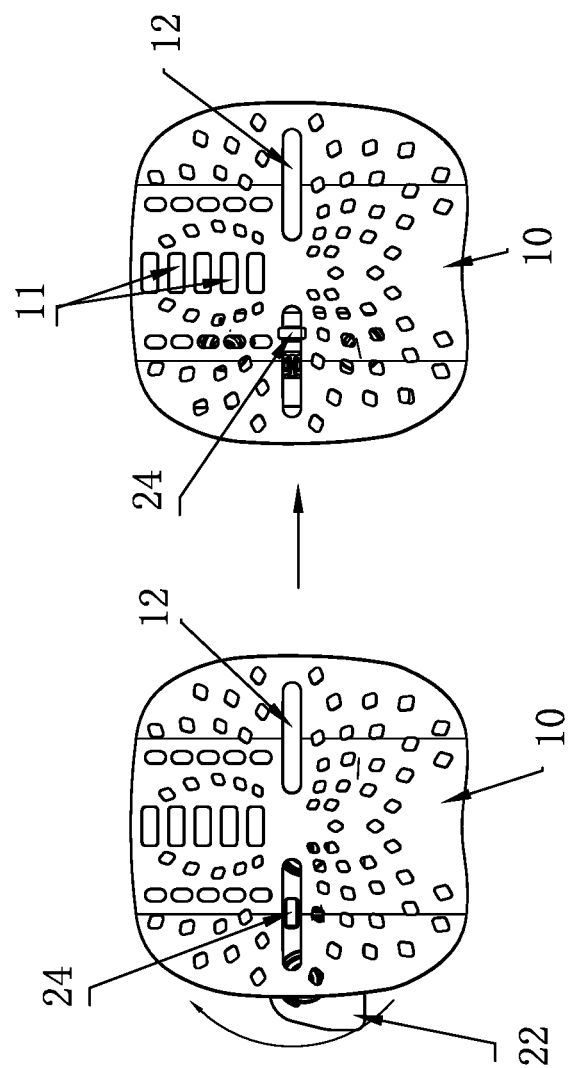
FIG. 10 is a front view of a combination of a connecting plate and a support board according to one example of the disclosure.

The first connecting plate 21 and the second connection plate 22 each comprise a sliding block 24 of fixed size and shape; the sliding block 24 comprises a first part and a second part which are combined to form a T-shaped structure; the first part is parallel to the long side of the corresponding connecting plate; the first part of the sliding block 24 has a length greater than the width of the groove 12 and has a width smaller than the width of the groove 12; in use, the sliding block 24 is inserted into the groove 12 and rotated 90 degrees in a counterclockwise or clockwise direction so as to be locked on the support board 10 (as shown in FIG. 10); as the sliding block 24 moves, the corresponding connecting plate moves horizontally along the groove 12 as well.

The support board 10 further comprises a locating mechanism that allows the first connecting plate 21 and the second connecting plate 22 to move to a limiting position.

2) Group of Pulleys

The first connecting plate 21 comprises a first group of pulleys and the second connecting plate 22 comprises a second group of pulleys. The drawstring comprises a first end and a second end; the first end of the drawstring is attached to a point; the drawstring is wrapped around the first group of pulleys and the second group of pulleys; and the second end of the drawstring is pulled tighten or loosened so that the first connecting plate 21 and the second connecting plate 22 are moved closer or farther away from each other.

In an alternative preferred embodiment of the disclosure, the first group of pulleys comprises a first upper group of pulleys 31 and a first lower group of pulleys 32 which are respectively disposed on the upper and lower parts of the first connecting plate; the second group of pulleys comprises a second upper group of pulleys 33 and a second lower group of pulleys 34 which are respectively disposed on the upper and lower parts of the second connecting plate. The first upper group of pulleys 31 is disposed opposite to the second upper group of pulleys 33; and the first lower group of pulleys 32 is disposed opposite to the second lower group of pulleys 34.

All of the pulleys have the same structure that comprises a first pulley 41 and a second pulley 42 having a smaller diameter than the first pulley 42; the first pulley 41 and the second pulley 42 are coaxially mounted around a shaft; the first pulley 41 and the second pulley 42 are disposed on a first shaft sleeve and a second shaft sleeve, respectively; and the first shaft sleeve has a greater diameter than the second shaft sleeve. An axial line of the first pulley 41 and the second pulley 42 is perpendicular to the direction of motion of the first connecting plate or the second connecting plate; the first pulley 41 is disposed close to the inner surface of the first connecting plate; and the second pulley 42 is disposed away from the inner surface of the first connecting plate.

Figure 8:
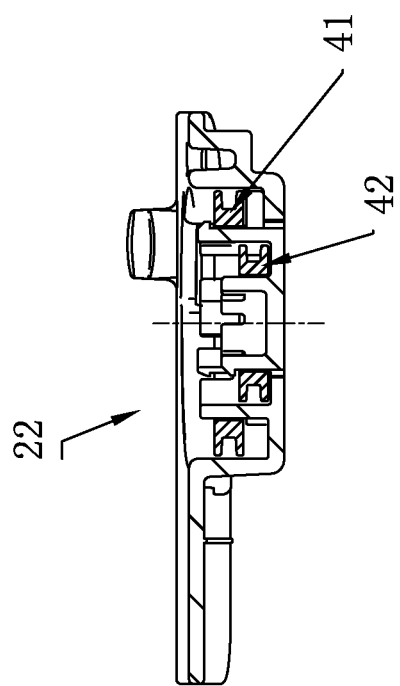
FIG. 8 is a sectional view taken from line C-C in FIG. 7B.
Figure 9:
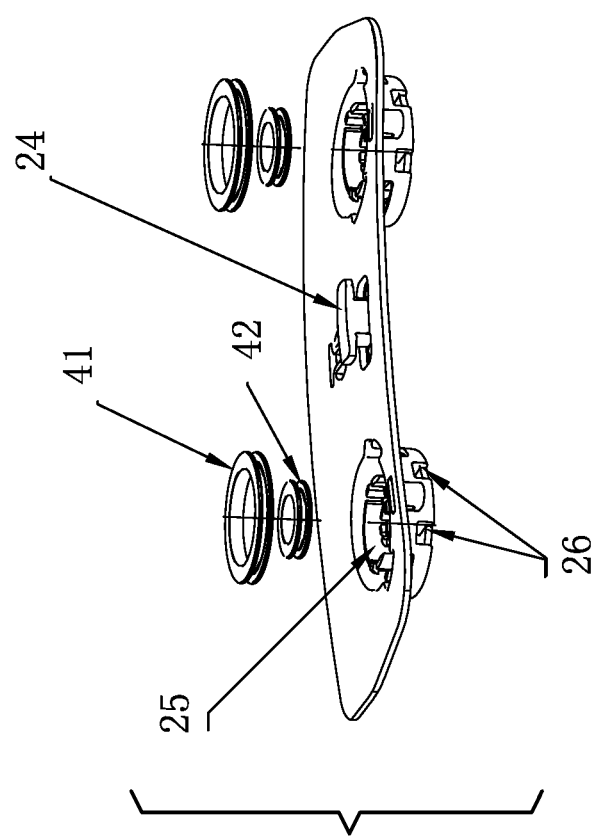
FIG. 9 is an exploded view of a combination of a group of pulleys and a connecting plate in FIG. 7A.

In an alternative preferred embodiment of the disclosure, each group of pulleys is disposed as follows (as shown in FIGS. 8 and 9).

Each connecting plate comprises an outer surface and an inner surface; the outer surface protrudes to form a cavity 25 and the cavity extends through the inner surface; a sidewall connects the inner surface and the outer surface; the first shaft sleeve and the second shaft sleeve are disposed in the cavity 25; and the sidewall, the first shaft sleeve, and the second shaft sleeve are integrally formed with or connected to the corresponding connecting plate.

The first pulley 41 is disposed into the first shaft sleeve and free to rotate around the first shaft sleeve; the second pulley 42 is disposed into the second shaft sleeve and free to rotate around the second shaft sleeve.

The first pulley 41 and the second pulley 42 each comprise a circle slot having an I-shaped cross section; the drawstring is wrapped around the circle slot.

The sidewall connecting the inner surface and the outer surface comprises a plurality of notches 26; the first end of the drawstring passes through the plurality of notches 26 so that the drawstring is wrapped around the first group of pulleys and the second group of pulleys. Each connecting plate further comprises a guide hole or guide groove 27 through which the second end of the drawstring is passed to control the direction of motion of the first connecting plate and the second connecting plate.

3) Drawstring

The drawstring is a braided rope that comprises a coating used to reduce friction during the drawstring-pulling process. The drawstring comprises a first drawstring 51 and a second drawstring 52 which pull tighten the first connecting plate and the second connecting plate, respectively.

The first drawstring 51 is wrapped around the first upper group of pulleys 31 and the second upper group of pulleys 33, and the second drawstring 52 is wrapped around the first lower group of pulleys 32 and the second lower group of pulleys 34; optionally, the first drawstring 51 is wrapped around the first lower group of pulleys 32 and the second lower group of pulleys 34, and the second drawstring 52 is wrapped around first upper group of pulleys 31 and the second upper group of pulleys 33.

Figure 6A:
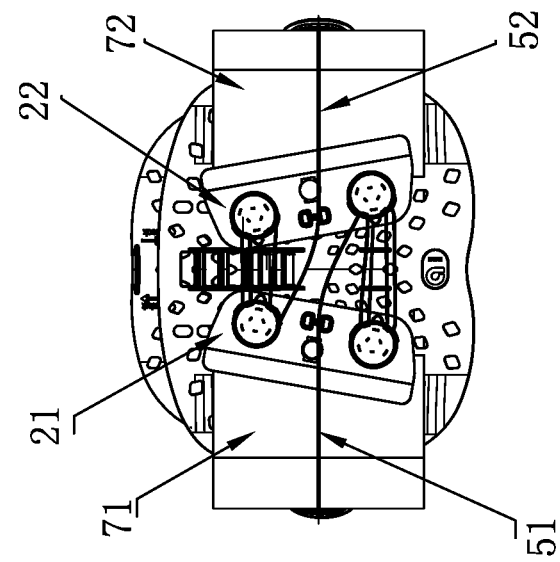
FIGS. 6A-6B are front views of a tightening structure in two tightening states.
Figure 6B:
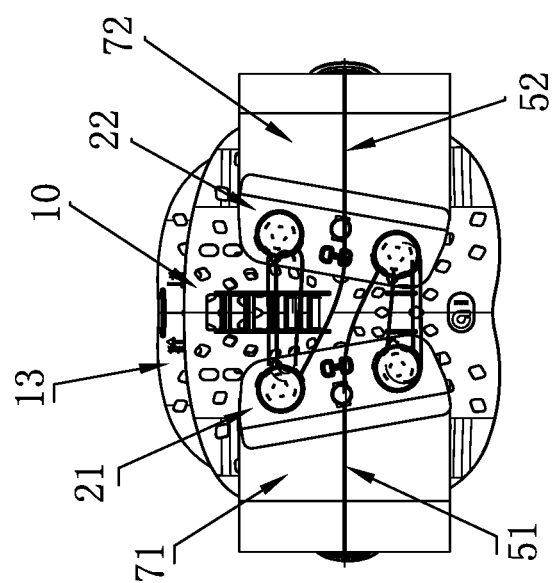

A first force is applied on the first drawstring and a second force is applied on the second drawstring; when the first force is equal to the second force, the first connecting plate is parallel to the second connecting plate; when the first force is greater than the second force, an A-shaped gap is formed between the first connecting plate and the second connecting plate; when the first force is less than the second force, a V-shaped gap is formed between the first connecting plate and the second connecting plate, as shown in FIGS. 6A-6B. The support board fits different body shapes and each connecting plates applies uniform force on the waist, thus enhancing user's experience.

The lumbar support belt further comprises a box 60 for receiving the second end of the drawstring; and the drawstring is wrapped inside the box 60 or released partially.

The box 60 comprises a bottom surface provided with a hook of a hook-loop fastener; the box 60 is attached to a loop of a hook-loop fastener on the outer surfaces of the first waist belt 71 and the second waist belt 72 to ensure the tightening mechanism is tight enough to grip the abdomen.

Figure 14:
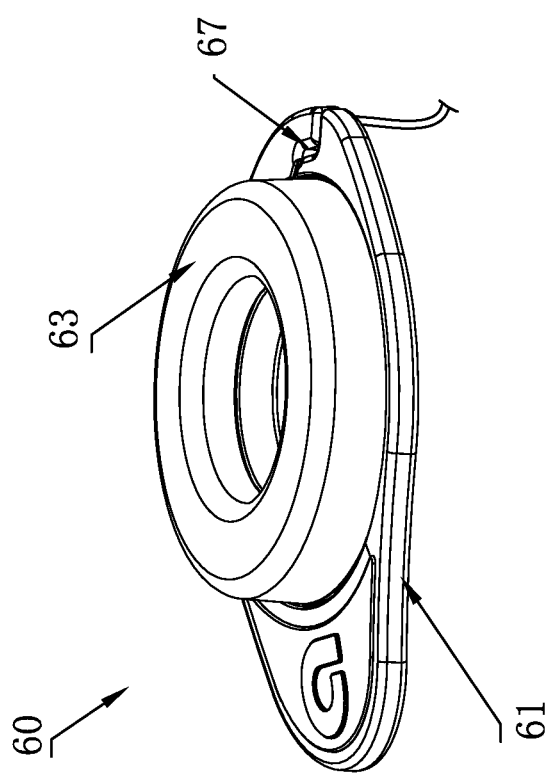
FIG. 14 is a perspective view of a box according to one example of the disclosure.
Figure 15:
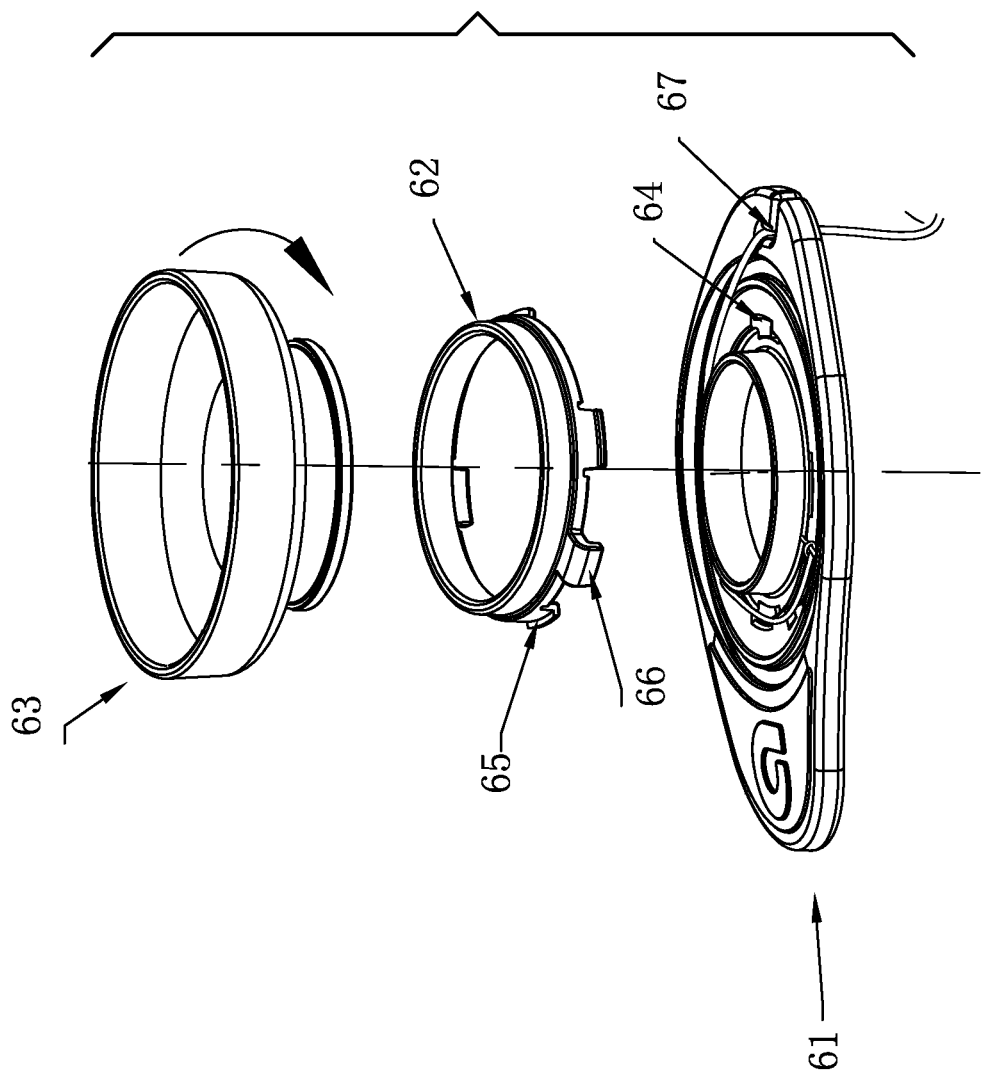
FIG. 15 is an exploded view of a box in FIG. 14.

The box 60 comprises a base 61, a fixing ring 62, and a rubber sleeve 63 (see FIGS. 14 and 15).

The base 61 comprises a central area and a cylindrical shaft sleeve extending radially from the central area; the cylindrical shaft sleeve comprises an outer periphery comprising a plurality of first holes 64 and a second hole; the plurality of first holes 64 is spaced apart from each other; the second hole is used to fix the second end of the drawstring; the fixing ring 62 is a hollow cylinder with open at both ends; one end of the fixing ring 62 comprises a plurality of clamping blocks 65 and a buckle 66 for fastening the second end of the drawstring; the plurality of clamping blocks 65 is locked in the corresponding plurality of first holes 64 and the buckle 66 is locked in the second hole; the rubber sleeve 63 comprises a first sleeve and a second sleeve disposed below the first sleeve; the first sleeve has a greater diameter than the second sleeve; the fixing ring 62 is disposed on the second sleeve and connected to the cylindrical shaft sleeve.

The drawstring is wrapped around the outer surface of the sidewall of the fixing ring 62; the box 61 further comprises a string hole 67 through which the second end of the drawstring is passed out of the box 61.

The rubber sleeve 63 further comprises a connecting part disposed between the first sleeve and the second sleeve; the first sleeve comprises a side wall surrounding an opening; the side wall of the first sleeve is pressed to make the opening face in the opposite direction, thus covering the drawstring wrapped around the fixing ring 62.

The drawstring is a braided rope that comprises a coating used to reduce friction during the drawstring-pulling process.

3. First Waist Belt 71 and Second Waist Belt 72

As shown in FIGS. 1, 2, and 3, the first waist belt 71 and the second waist belt 72 each comprise a first part and a second part sewn onto the first part; the first part comprises a first stretch fabric 74 that can undergo large deformation; and the second part comprises a second stretch fabric 75 that can undergo small deformation.

1) First Stretch Fabric 74

In an alternative preferred embodiment of the disclosure, the stretch fabric has a composite layer comprising an outer layer, a middle layer, and an inner layer; the outer layer comprises a stretch fabric provided with a loop of a hook-loop fastener; the middle layer comprises a fabric which can be compressed or extended; and the inner layer comprises a stretch fabric which is skin-friendly and sweet-absorbing.

The loop of the outer layer is attached to the hook on the bottom surface of the box; to say that the middle layer "can be extended" means that the fabric has tensile strength in warp and weft directions; to say that the middle layer "can be compressed" means that the fabric is elastic in the vertical direction when compressed; when the drawstring is pulled tighten, the local pressure generated by the drawstring is reduced due to the elasticity of the middle layer, thus enhancing user's experience.

In an alternative preferred embodiment of the disclosure, the composite layer comprises:
  an inner layer comprising velvet, such as a Nylon+ spandex fabric, offering advantages such as safe for skin, sweat absorption, anti-skid surface, and high elasticity;
  a middle layer comprising a sponge with holes; when the drawstring is pulled tighten, the local pressure generated by the drawstring is reduced due to the elasticity of the sponge, thus keeping the waist comfortable; and the holes in the sponge makes the lumbar support belt breathable; and
  an outer layer comprising a stretch fabric provided with a loop of a hook-loop fastener; and the loop is attached to the hook on the bottom surface of the box.

2) Second Stretch Fabric 75

The second stretch fabric employs a stretch fabric having a smaller elastic deformation than the first stretch fabric, which is widely used in conventional support belts.

3) Characteristics of the First Stretch Fabric and the Second Stretch Fabric

The first stretch fabric 74 is an elastic material that is wrapped to support waist without restricting movement of core muscles in the abdomen and waist, thus preventing diseases such as muscle atrophy caused by stiffness resulting from inactivity.

The second stretch fabric 75 is a tight material that keeps the first waist belt 71 and the second waist belt 72 around the waist and prevents the lumbar support belt from slipping off.

The first waist belt 71 and the second waist belt 72 each comprise a side part and a front part; the first stretch fabric 74 is disposed on each side part to cover both sides of the waist; and the second stretch fabric 75 is disposed on each front part to cover the abdomen.

The two front parts comprises a hook and a loop of a hook-loop fastener, respectively; in use, the support board 10 and the tightening mechanism are aligned with the back waist; the front parts of the first waist belt 71 and the second waist belt 72 are attached together to form a compression belt 73, and thus the lumbar support belt is wrapped around the waist to cover the abdomen and the both sides of the waist.

4) Belt Cutting Template 76

The lumbar support belt further comprises a belt cutting template used in combination to cut an overlong part on one side of the first waist belt 71 or the second waist belt 72.

Figure 12:
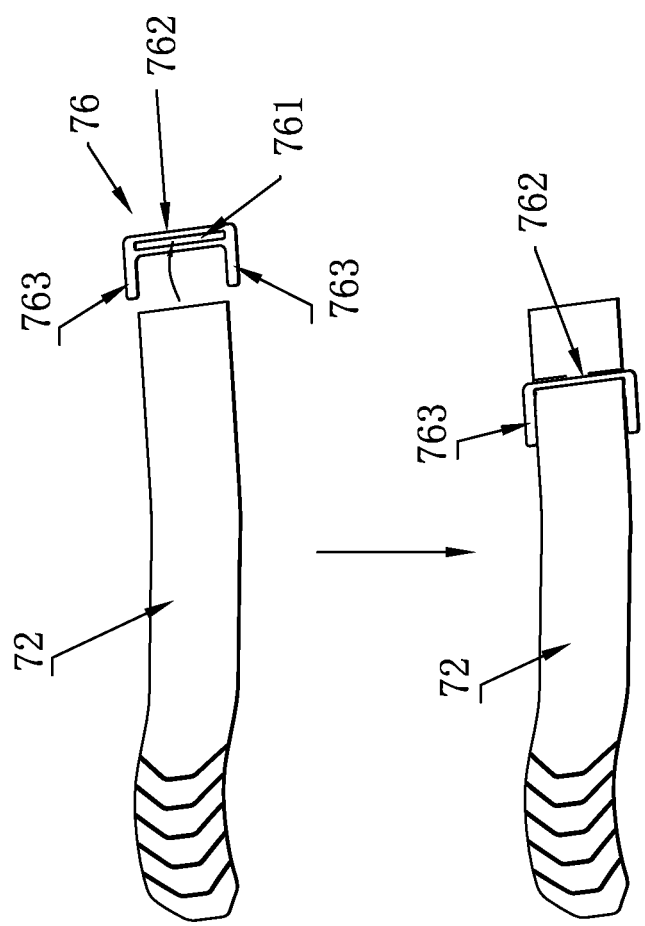
FIG. 12 is a perspective view of a belt cutting template according to one example of the disclosure.

As shown in FIG. 12, the belt cutting template is a plastic board that comprises a hole 761, a cutting side 762, and two reference sides 763. In use, one end of the first waist belt or the second waist belt is inserted into the hole 761; the belt cutting template moves to a preset position at which the cutting side 762 and the two reference sides 763 are aligned with the edges of the first waist belt or the second waist belt; and a pair of scissors cuts an overlong part of each waist belt along the cutting side, thus making the cutting edge neat and straight.

4. Abdominal Compression Board 80

The abdominal compression board used to keep the post in a straight up right position and protect the lumbar vertebrae; as the tightening mechanism is tightened, the compression belt 73 and the support board respectively apply a uniform force on the abdomen and the back waist to support the waist.

Figure 11:
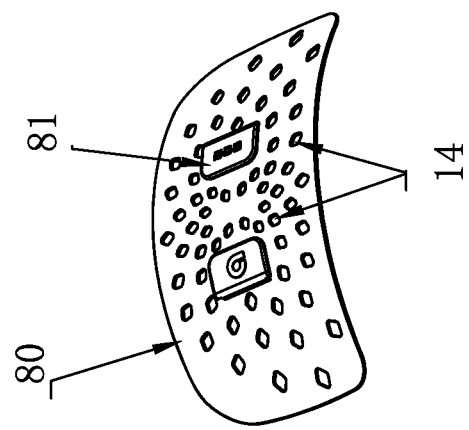
FIG. 11 is a perspective view of an abdominal compression board according to one example of the disclosure.
Figure 11:
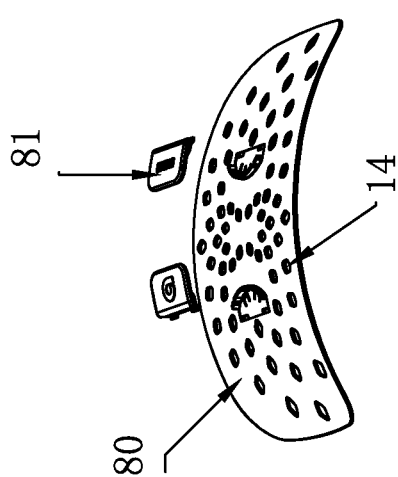

The abdominal compression board 80 is an arc-shaped rigid plastic plate comprising a plurality of holes (as shown in FIG. 11).

The first waist belt 71 or the second waist belt 72 comprises a pocket on the front part; in use, the abdominal compression board 80 is inserted into the pocket; the first waist belt 71 is attached to the second waist belt 72 to form the compression belt 73; and a central axis of the abdominal compression board 80 is aligned with a vertical line running through the center of the belly button. In an alternative preferred embodiment of the disclosure, the first waist belt 71 is attached to the second waist belt 72 to form the compression belt 73 through a hook-loop fastener.

The first drawstring and the second drawstring 52 are pulled to control the force of the support board 10 and the abdominal compression board 80 on the lumbar vertebrae and the abdomen.

The lumbar support belt further comprises a wire hinge 81 disposed on each end of the abdominal compression board 80; the drawstring is wrapped around the wire hinge 81 and easily pulled to control the tightening mechanism.

It will be obvious to those skilled in the art that changes and modifications may be made, and therefore, the aim in the appended claims is to cover all such changes and modifications.

What is claimed is:

1. A lumbar support belt, comprising:
a back belt;
a first waist belt;
a second waist belt;
a tightening mechanism;
a first drawstring; and
a second drawstring;
wherein:
the first waist belt and the second waist belt are connected to two ends of the back belt, respectively, and configured to be wrapped around a waist and an abdomen of a user;
the first waist belt and the second waist belt are adjustable in length;
the back belt is a support board being plastic; the support board comprises a first horizontal groove, a second horizontal groove, and a central transversal axis; the first horizontal groove and second horizontal groove extend along a horizontal plane; the central transversal axis extends along a central transversal plane; the central transversal axis and the central transversal plane are substantially perpendicular to the horizontal plane; the first horizontal groove and the second horizontal groove are disposed substantially symmetrically about the central transversal plane;
the first waist belt comprises a first front part and the second waist belt comprises a second front part; the first front part and the second front part are attached to each other to form a compression belt configured for abutting against the abdomen of the user;
the first waist belt comprises a first back part and the second waist belt comprises a second back part; the first back part and the second back part are disposed at a distance from the support board; the first back part and the second back part are connected to the support board through the tightening mechanism; and
the lumbar support belt is configured to be wrapped around the waist, the tightening mechanism is configured to be tightened or loosened to control the support board and the compression belt to press the waist and abdomen;
the tightening mechanism comprises a first connecting plate and a second connecting plate which are of a same shape and have a same curvature as the support board;
the first connecting plate comprises a first fixed end and a first free end;
the first fixed end is connected to one end of the first waist belt; the first connecting plate comprises an inner surface comprising a first sliding block; the first sliding block is disposed into the first horizontal groove and is configured to slide back and forth to drive the first connecting plate to move horizontally with respect to the support board; the first connecting plate further comprises a first group of pulleys;
the second connecting plate comprises a second fixed end and a second free end; the second fixed end is connected to one end of the second waist belt; the second connecting plate comprises an inner surface comprising a second sliding block; the second sliding block is disposed into the second horizontal groove and is configured to slide back and forth to drive the second connecting plate to move horizontally with respect to the support board; the second connecting plate further comprises a second group of pulleys;

the first drawstring and the second drawstring are wrapped around the first group of pulleys and the second group of pulleys; whereby when the first drawstring or the second drawstring is pulled tight, the first connecting plate and the second connecting plate move towards each other;

the first group of pulleys comprises a first upper group of pulleys and a first lower group of pulleys; the first upper group of pulleys and the first lower group of pulleys are disposed on an upper part and a lower part of the first connecting plate, respectively;

the second group of pulleys comprises a second upper group of pulleys and a second lower group of pulleys; the second upper group of pulleys and the second lower group of pulleys are disposed on an upper part and a lower part of the second connecting plate, respectively;

the first drawstring is wrapped around the first upper group of pulleys and the second upper group of pulleys to pull tight or loosen the upper part of the first connecting plate and the upper part of the second connecting plate; whereby the distance between the upper part of the first connecting plate and the upper part of the second connecting plate is adjusted by the first drawstring; and the second drawstring is wrapped around the first lower group of pulleys and the second lower group of pulleys to pull tight or loosen the lower part of the first connecting plate and the lower part of the second connecting plate; whereby the distance between the lower part of the first connecting plate and the lower part of the second connecting plate is adjusted by the second drawstring.

2. The belt of claim 1, wherein each of the first upper group of pulleys, the first lower group of pulleys, the second upper group of pulleys, and the second lower group of pulleys comprise a first pulley and a second pulley having a smaller diameter than the first pulley; the first pulley and the second pulley are coaxial; an axial line of the first pulley and the second pulley is perpendicular to the direction of motion of the first connecting plate or the second connecting plate; each connecting plate comprises an outer surface and an inner surface; the outer surface protrudes to form a cavity and the cavity extends through the inner surface; a sidewall connecting the inner surface and the outer surface comprises a plurality of notches; the first drawstring or the second drawstring comprises a first end and a second end; and the second end of the first drawstring or the second drawstring passes through at least one of the plurality of notches on the first connecting plate and the second connecting plate so that the first drawstring or the second drawstring is wrapped around the first group of pulleys and the second group of pulleys.

3. The belt of claim 2, wherein the lumbar support belt further comprises a height-adjustable board disposed on the support board; the support board further comprises a plurality of locating holes spaced apart from each other; the height-adjustable board comprises at least one locating block; the at least one locating block is inserted into the plurality of locating holes to adjust a height of the height-adjustable board relative to the support board.

4. The belt of claim 3, wherein the lumbar support belt further comprises a box for receiving; the first drawstring or the second drawstring; the first end of the first drawstring or the second drawstring is secured to the box; the box comprises a bottom surface provided with a hook of a hook-loop fastener; each of the first waist belt and the second waist belt comprises an outer surface provided with a loop of the hook-loop fastener; and the hook of the box is attached to the loop of one of the first waist belt and the second waist belt.

5. The belt of claim 4, wherein the lumbar support belt further comprises a wire hinge disposed on each end of the compression belt to control the tightening mechanism.

6. The belt of claim 5, wherein the support board, the abdominal compression board, and the height-adjustable board each comprise a plurality of vent holes.

7. The belt of claim 6, wherein the support board further comprises an inner surface comprising an airbag cushion.

8. The belt of claim 1, wherein an abdominal compression board is attached to the compression belt.

9. The belt of claim 8, wherein each of the first waist belt and the second waist belt comprises a first part and a second part sewn onto the first part; the first part comprises a first stretch fabric; the second part comprises a second stretch fabric; an elastic deformation of the first stretch fabric is larger than that of the second stretch fabric; and the compression belt employs the second stretch fabric.

10. The belt of claim 9, wherein the lumbar support belt further comprises a belt cutting template used in combination with a pair of scissors to cut an overlong part of the first waist belt and the second waist belt.

\* \* \* \* \*